United States Patent
Pedroza-Islas

(10) Patent No.: US 9,974,315 B2
(45) Date of Patent: May 22, 2018

(54) MICROENCAPSULATED BACTERIAL CONSORTIUM FOR THE DEGRADATION OF GLUTEN INTO SOURDOUGH AND METHOD FOR PRODUCING SAID SOURDOUGH

(71) Applicant: Javier Gonzalez-De La Torre, Jalisco (MX)

(72) Inventor: Ruth Pedroza-Islas, México (MX)

(73) Assignee: Javier Gonzalez-De La Torre, Jalisco (MX)

( * ) Notice: Subject to any disclaimer, the term of this patent is extended or adjusted under 35 U.S.C. 154(b) by 0 days. days.

(21) Appl. No.: 14/382,369

(22) PCT Filed: Nov. 6, 2012

(86) PCT No.: PCT/IB2012/002254
§ 371 (c)(1),
(2) Date: Sep. 2, 2014

(87) PCT Pub. No.: WO2014/072758
PCT Pub. Date: May 15, 2014

(65) Prior Publication Data
US 2015/0140167 A1 May 21, 2015

(51) Int. Cl.
| | | |
|---|---|---|
| *A21D 8/04* | (2006.01) | |
| *C12N 1/20* | (2006.01) | |
| *A21D 13/066* | (2017.01) | |
| *C12N 1/04* | (2006.01) | |
| *A23L 29/00* | (2016.01) | |
| *A23L 7/104* | (2016.01) | |
| *A23L 33/135* | (2016.01) | |
| *A23P 10/30* | (2016.01) | |

(52) U.S. Cl.
CPC ............ *A21D 8/045* (2013.01); *A21D 8/042* (2013.01); *A21D 13/066* (2013.01); *A23L 7/104* (2016.08); *A23L 29/06* (2016.08); *A23L 29/065* (2016.08); *A23L 33/135* (2016.08); *C12N 1/04* (2013.01); *C12N 1/20* (2013.01); *A23P 10/30* (2016.08); *A23V 2002/00* (2013.01); *A23Y 2220/13* (2013.01); *A23Y 2220/67* (2013.01); *A23Y 2220/81* (2013.01)

(58) Field of Classification Search
CPC ................................. A21D 8/045; A21D 8/042
USPC .......................................................... 426/61
See application file for complete search history.

(56) References Cited

U.S. PATENT DOCUMENTS

| 7,037,708 B1 * | 5/2006 | Runge .............. C12N 1/04 424/93.4 |
|---|---|---|
| 2004/0247581 A1 | 12/2004 | Bronstad et al. |
| 2008/0131556 A1 * | 6/2008 | De Simone ............ A21D 8/042 426/20 |
| 2008/0299258 A1 | 12/2008 | Roman et al. |
| 2009/0214647 A1 | 8/2009 | Chen et al. |
| 2012/0034339 A1 * | 2/2012 | Giuliani ................ A21D 8/042 426/20 |

FOREIGN PATENT DOCUMENTS

| JP | 2009-511506 | 3/2009 |
|---|---|---|
| JP | 2009-543576 | 12/2009 |
| JP | 2012-175977 | 9/2012 |
| WO | 02065842 A1 | 8/2002 |
| WO | 2006/097415 | 9/2006 |
| WO | 2007/050656 | 5/2007 |
| WO | 2008/010252 | 1/2008 |
| WO | 2010073283 A2 | 7/2010 |

OTHER PUBLICATIONS

Anal, A. K. et al. Trends in Food Sci. Technol. 18: 240-251 (2007).*
Di Cagno, R. et al. Appl. Environ. Microbiol., 2002. 68: 623-633.*
Di Cagno Raffaella et al., "Use of selected sourdough strains of Lactobacillus for removing gluten and enhancing the nutritional properties of gluten-free bread", Journal of Food Protection, pp. 1491-1495, vol. 71, No. 7 (Jul. 2008).
Greco L et al., "Safety for Patients With Celiac Disease of Baked Goods Made of Wheat Flour Hydrolyzed During Food Processing", Clinical Gastroenterology and Hepatology, pp. 24-29, vol. 9, No. 1 (Jan. 2011).
Rizzello, Cg, et al., "Highly Efficient Gluten Degradation by Lactobacilli and Fungal Proteases during Food Processing: New Perspectives for Celiac Disease", Applied and Environmental Microbiology, pp. 4499-4507, vol. 73, No. 14 (Jul. 2007).
Angelis, et al., Mechanism of Degradation of Immunogenic Gluten Epitopes from *Triticum turgidum* L. var. durum by Sourdough Lactobacilli and Fungal Proteases, Applied and Environmental Microbiology, Jan. 2010, pp. 508-518, vol. 76, No. 2.
Chavan, et al., Sourdough Technology—A Traditional Way for Wholesome Foods: A Review, Comprehensive Reviews in Food Science and Food Safety, 2011, pp. 170-183, vol. 10.

* cited by examiner

*Primary Examiner* — Hamid R Badr
(74) *Attorney, Agent, or Firm* — Browdy and Neimark, P.L.L.C.

(57) ABSTRACT

The present invention is related to a microencapsulated bacterial consortium for gluten degradation, which comprises: a) three different strains of commercially available lactic-acid bacteria; b) encapsulating agents; c) prebiotics; and d) trehalose; in combination with a proteolytic enzyme of bacterial origin and a proteolytic enzyme of fungal origin. Preferably, the microencapsulated bacterial consortium comprises: a) *Lactobacillus plantarum* ATCC 8014; b) *Lactobacillus sanfranciscensis* ATCC 27652; c) *Lactobacillus brevis* ATCC 14869; d) isolated protein from milk serum with 90% protein; e) maltodextrin with a dextrose equivalent of 10; f) arabic gum; g) maguey honey; and h) trehalose; in combination with a protease of bacterial origin and a protease of fungal origin. It also describes a process for obtaining the microencapsulated bacterial consortium, as well as the preparation of sourdoughs therefrom, and the use of said sourdoughs to obtain baking products.

18 Claims, No Drawings

MICROENCAPSULATED BACTERIAL CONSORTIUM FOR THE DEGRADATION OF GLUTEN INTO SOURDOUGH AND METHOD FOR PRODUCING SAID SOURDOUGH

FIELD OF THE INVENTION

The present invention is related to the food industry for making bread and its derivatives, and more particularly it relates to a bacterial consortium for gluten degradation in sourdoughs and the process of making thereof, as well as to the making of bakery products using said gluten-free sourdoughs.

BACKGROUND OF THE INVENTION

Celiac disease is an immune system disorder, genetic in origin, induced by gluten consumption, which is a protein found present in wheat, rye and barley. This is poorly digested in the human upper gastrointestinal tract. Gluten is composed of two fractions, gliadin and glutenin. Gliadins are alcohol soluble and contain the largest amount of toxic components for celiac patients (Green, P. H. R. and Cellier, C. 2007. Celiac disease. N. Engl. J. Med.; 357:1731-1743).

When a patient with celiac disease eats some gluten-containing food, their immune system responds in such a way that damages or destroys the intestinal villi, causing the food nutrients to be non-absorbed, thereby leading to a poor nutrition. The symptoms of celiac disease vary depending on the age of the patient, in children being the most common diarrhea, abdominal distension, vomiting and weight loss, while in adults the prevailing symptoms are iron-deficiency anemia, fatigue, bone pain, arthritis, osteoporosis, among others (National Digestive Diseases Information Clearinghouse, NIH Publication No. 08-4269, 2008).

Until recently, celiac disease was considered a rare disease, but currently it is one of the most common intolerances, having a global incidence of 1 in every 150 newborns, and it is estimated that only 9% is diagnosed. According to numbers provided by the National Institute of Medical Sciences and Nutrition (Instituto Nacional de Ciencias Médicas y Nutrición) Salvador Zubirán, in Mexico, there is an approximate volume of 2.6 million potential celiac patients (http://celiacosdemexico.org.mx/manifiesto-celiaco).

Currently, the only accepted treatment for celiac disease is a gluten-free diet for life. According to the Codex Alimentarius, it is considered that a food is gluten-free when the gluten concentration therein is less than 20 ppm. However, this represents negative nutritional implications such as a decreased intake of polysaccharides and thus lower energy intake, a reduction in beneficial intestinal flora for human health and an increase in the presence of opportunistic pathogens. Beneficial flora reduction by the gluten-free diet negatively affects immunostimulating activity and decreases the production of anti-inflammatory compounds.

Therefore, there is a need to have gluten-free products, suitable for consumption by celiac patients and, accordingly, allowing them to improve their diet by having a greater variety of foodstuffs at hand.

One of the most important products in the daily diet of human beings is bread, manufactured mainly from wheat flour.

The properties of the wheat dough depend primarily on gluten proteins. In recent years, diverse treatments have been applied to improve the quality of these proteins or to improve the gas retention process to produce a more aerated bread (Arendt et al., 2007. Impact of sourdough on the texture of bread. Food Microbiology 24:165-174). One of these processes is the production of bread using sourdoughs.

The main function of this process is to leaven the dough to produce a higher gas content and therefore a fluffier bread having softer crumbs.

Sourdough is obtained with a fermented mixture of flour (wheat, oat and rice, etc.) and water with yeast and lactic acid bacteria (LAB) usually belonging to the genus *Lactobacillus* (De Vuyst, L. and Vancanneyt, M. 2007. Biodiversity and identification of sourdough lactic acid bacteria. Food Microbiology 24.120-127). The use of sourdoughs offers great advantages in good baking technology, for example, pH decrease during fermentation, better gas retention, higher resistance of the gluten network, inhibition of fluor amylases, binding of water with gluten and starch granules, swelling of pentoses, solubilization of phytate complex and prevention of a poor fermentation (Di Cagno, R. et al. 2002. Proteolysis by sourdough lactic acid bacteria: Effects on wheat Flour protein fractions and gliadin peptides involved in human cereal intolerante. Applied and Environmental Microbiology 68: 623-633). These sourdoughs are admixed with fresh dough for bread making.

In addition, the LAB used in fermentation with sourdoughs allows gluten modification during bread elaboration, thereby allowing the removal of protein fractions that are toxic for celiac patients. However, not all the lactic acid bacteria can decrease the gluten residual concentration to doses capable of being tolerated by gluten-intolerant people (celiac patients), whereby it is necessary to select the LAB type and to find a suitable combination there between, by using proteases co-adjuvating in gluten hydrolysis.

During fermentation, the LAB proteolytic system releases low molecular weight peptides and amino acids, promoting the metabolic activity of microorganisms, contributing to achieving a better flavor and reducing the content of allergenic peptides (De Angelis, M. et al. 2005. VSL #3 probiotic preparation has the capacity to hydrolyze gliadin polypeptides responsable for Celiac Sprue probiotics and gluten intolerante. Biochimica et Biophysica Acta 1762(1): 80-93), which opens a great hope for celiac patients sensitive to the gliadin fraction, reason why they have been prevented from ingesting products containing even small amounts of gluten (Wieser, H. 2007. Chemistry of Gluten proteins. Food Microbiology 24: 115-119; Di Cagno et al., 2002). Studies carried out in bread making from sourdough showed that the LAB, under specific processing conditions (long time fermentation and semi-liquid), have the ability to hydrolyse the wheat gliadin fraction (Di Cagno, R. et al. 2004. Sourdough bread made from wheat and nontoxic flours and started with selected *lactobacilli* is tolerated in celiac sprue patients. Applied and Environmental Microbiology 70(2):1088-1096.; De Angelis et al., 2005).

Rizzello et al., (Highly efficient gluten degradation by *lactobacilli* and fungal proteases during food processing: new perspectives for celiac disease. Applied and Environmental Microbiology 73 (14): 4499-4507, 2007) used mixtures of non-commercial strains of *Lactobacilli* (previously selected based on their ability to hydrolyze gliadins) with fungal origin proteases in different combinations, in sourdoughs to remove wheat flour toxicity during a relatively long fermentation. It was noted that hydrolysis kinetics by *Lactobacilli* was highly efficient, further, the proteins extracted from the sourdough induced interferon γ activation; the albumins, globulins and gliadins were completely hydrolyzed, while 20% of the glutenins remained in the sourdough.

Likewise, US Patent Application No. US 2008/0131556 describes a mixture of at least six commercially available LAB and/or *bifidobacteria* species. This mixture can be used in the preparation of sourdoughs. Similarly, when a sufficient amount of microbial proteases commonly used in bakery is added to these formulations, the fermented sourdough has a gluten concentration lower than 200 ppm, which might be non-appropriate for the consumption by a celiac patient. Likewise, the mixture to achieve this degradation is complex because it is necessary to use a large number of species, since the more LAB species are used, the higher degradation of gliadins is seen.

On the other hand, International Publication No. WO 2010/073283 describes a mixture comprising two types of LAB, in combination with one or more fungal proteases. After a 12 h fermentation, no traces of gliadin and glutenin were detected. In addition, the gluten residual concentration was less than 20 ppm.

As can be seen, bacterial cultures already known in the prior art for gluten degradation present certain disadvantages, such as the use of LAB complex mixtures (of at least six species) in the case of commercially available strains, or the use of specifically selected strains, involving the need to activate, reproduce, wash and add the culture in suspension (inoculum) to the dough, requiring daily preparation thereof and a highly specialized management to prevent contamination, keeping it active in the same growing stage and in the proper ratio between LAB species and in a sufficient amount, which represents a latent risk of contamination.

An alternative to reduce the difficulties related to the inoculum elaboration each time this is required is to microencapsulate it in order to produce a sufficient amount, involving a reduction in culture handling, thereby reducing risks related to contamination and viability of the lactic-acid cultures and promoting process efficiency for the degradation of wheat doughs.

The LAB viability and activity is determined by a series of factors, including the rate of culture multiplication, lactic and acetic acid production capacity, total solid content, temperature and time of incubation, amount of inoculum used, and antibiotic, disinfectant or detergent residues (Picot and Lacroix, 2003; Briceño 2005; Desmond et al., 2002; Favaro-Trinidad and Grosso, 2002; Lian et al., 2003; Akalin et al., 2004; Cerdeira et al., 2005; Iyer and Kailasapathy, 2005; Ozer et al., 2005; Ann et al., 2007).

There are different methods to increase prebiotic bacteria resistance to adverse conditions, for example, microencapsulation and incorporation of micro-nutrients with prebiotic function (Picot and Lacroix, 2003; Chandramouli et al., 2004; Talwalkar and Kailasapathy, 2004; Cerdeira et al., 2005; Iyer and Kailasapathy, 2005; Ann et al., 2007).

Microencapsulation has been proposed to increase prebiotics viability, since their sensitivity to the oxygen high levels, manufacturing, storage, freezing, acidic or alkaline conditions during the passing through the gastrointestinal tract may be protected (Favaro-Trinidad and Grosso, 2002; Picot and Lacroix, 2003; Chandramouli et al., 2004; Iyer and Kailasapathy, 2005; Crittenden et al., 2006; Ann et al., 2007).

Even when the microencapsulation of LAB is already known in the state of the art, in order to ensure good protection for the materials to be encapsulated, which will be used during sourdough fermentation to degrade the gluten, it is essential to make a good selection of the drying conditions as well as of the encapsulating media, which is not described in the state of the art, since the micro-capsule wall design is a critical point performed depending on the specific type of material to be protected, the environment the micro-capsules should be applied on, and the release mechanism of the active material they protect.

OBJECTS OF THE INVENTION

Considering the drawbacks of the prior art, it is an object of the present invention to provide a microencapsulated microbial consortium of LAB strains, which in combination with a proteolytic enzyme of bacterial origin and a proteolytic enzyme of fungal origin, results appropriate for the production of sourdoughs, further being stable, of fast activation and of easy handling, to be directly added to the wheat dough to degrade the gluten, including the toxic fractions for celiac patients.

Moreover, it is another object of the present invention to obtain sourdoughs, wherein the gluten is degraded, using the above-mentioned microencapsulated microbial consortium, and through a process being simple and that can be used at an industrial scale.

An additional object of the present invention is to obtain a baking product from sourdoughs, which as a result is gluten-free and suitable for consumption by patients with celiac disease.

SUMMARY OF THE INVENTION

To that end, a microencapsulated bacterial consortium has been developed for gluten degradation, comprising: a) three different strains of commercially available lactic acid bacteria; b) encapsulating agents; c) prebiotics; and d) trehalose; in combination with a proteolytic enzyme of bacterial origin and a proteolytic enzyme of fungal origin.

Other aspects of the invention consider a process for obtaining the microencapsulated bacterial consortium for gluten degradation; a sourdough made from said bacterial consortium, in combination with a bacterial origin protease and a fungal origin protease, and which has a gluten concentration lower than 20 ppm; the making method of the sourdough and a gluten-free baking product obtained from the sourdough.

DETAILED DESCRIPTION OF THE INVENTION

During the development of the present invention, it was unexpectedly found that a microencapsulated bacterial consortium comprising three different strains of commercially available lactic acid bacteria; encapsulating agents to provide a high level of protection to the bacterial consortium, and fast dissolution in the wheat dough system so that its activity starts quickly; prebiotics to achieve the highest survival of the consortium; and, trehalose as a specific nutritional ingredient of the bacteria they integrate, when used in combination with a proteolytic enzyme of bacterial origin and a proteolytic enzyme of fungal origin, both also commercially available, is useful for gluten degradation during the sourdough fermentation process.

Preferably, lactic-acid bacteria strains are *Lactobacillus plantarum* ATCC 8014, *Lactobacillus sanfranciscensis* ATCC 27652 and *Lactobacillus brevis* ATCC 14869.

Encapsulating agents are selected from the group comprising isolated protein from milk serum with 90% protein, maltodextrin with a dextrose equivalent of 10, arabic gum, mesquite gum, sodium alginate, pectin, soy isolated protein, casein and combinations thereof, preferably isolated protein from milk serum with 90% protein, maltodextrin with a dextrose equivalent of 10, arabic gum and combinations thereof.

On the other hand, prebiotics are selected from the group comprising polydextrose, inulin and maguey honey, preferably maguey honey.

With respect to the proteolytic enzyme of bacterial origin and the proteolytic enzyme of fungal origin, these are selected from enzymes commonly used for baking.

In a specific embodiment of the invention, the microencapsulated bacterial consortium comprises: (a) *Lactobacillus plantarum* ATCC 8014; b) *Lactobacillus sanfranciscensis* ATCC 27652; c) *Lactobacillus brevis* ATCC 14869; d) isolated protein from milk serum with 90% protein; e) maltodextrin with a dextrose equivalent of 10; f) arabic gum; g) maguey honey; and h) trehalose; in combination with a proteolytic enzyme of bacterial origin and a proteolytic enzyme of fungal origin.

More preferably, the microencapsulated bacterial consortium comprises: a) *Lactobacillus plantarum* ATCC 8014; b) *Lactobacillus sanfranciscensis* ATCC 27652; c) *Lactobacillus brevis* ATCC 14869; d) from 40 to 60% of isolated protein from milk serum with 90% protein; e) from 10 to 20% of maltodextrin with a dextrose equivalent of 10; f) from 20 to 80% of arabic gum; g) from 1 to 10% of maguey honey; and h) from 0.5 to 5% of trehalose; in combination with 0.005 to 0.03% of a proteolytic enzyme of bacterial origin and 0.001 to 0.02% of a proteolytic enzyme of fungal origin.

The microencapsulating is carried out by processes well-known in the state of the art, such as spray-drying. For example, the bacterial consortium microencapsulated can be obtained according to the following:

a) separately reactivate each strain of lactic-acid bacteria;
b) when each strain is active, separately culturing in a liquid culture medium until reaching each strain desired concentration;
c) for each strain, removing the excess culture medium to concentrate the microorganisms, preferably by centrifugation, obtaining a pellet;
d) separately, resuspending the pellet obtained for each strain in saline suspension and adjusting to the required volume;
e) mixing the necessary amounts of each strain and take to a final volume;
f) dissolve the encapsulating agents in water, at the proper ratios to have 20 to 30% of dissolved solids;
g) adding prebiotics and trehalose;
h) inoculate the mixture of three strains of lactic-acid bacteria, such that about $10^{10}$ CFU of said mixture of three strains of lactic-acid bacteria per gram of powder microencapsulated is obtained; and
i) drying, preferably with a spray-dryer, to an inlet temperature of between 110 and 160° C., and an outlet temperature of between 60 and 80° C., with a feed rate between 20 and 50 mL/min.

Preferably, in step e), *Lactobacillus plantarum* ATCC 8014 is mixed at a ratio from 10 to 50%, *Lactobacillus sanfranciscensis* ATCC 27652 in a ratio of 40%, and *Lactobacillus brevis* ATCC 14869 at a ratio from 10 to 50%.

Preferably, the drying is carried out using a spray-dryer, at an inlet temperature of 150° C., and an outlet temperature of 80° C., with a feed rate of 22 mL/min.

Another aspect of the invention considers a sourdough made from the microencapsulated bacterial consortium of the present invention, in combination with a proteolytic enzyme of bacterial origin and a proteolytic enzyme of fungal origin, and wherein the sourdough has a gluten concentration of less than 20 ppm, preferably less than 10 ppm, being suitable for the preparation of gluten-free baking products.

Preferably, this gluten concentration in the sourdough is achieved after at least 3 hours of fermentation, more preferably after 31 hours of fermentation.

The process of making sourdoughs of the present invention comprises the following steps:

i) mixing 30 to 60% of flour with 40 to 80% of water to obtain a dough with a dough yield from 150 to 475, preferably from 150 to 160;
ii) adding 0.005 to 0.03% of proteolytic enzyme of bacterial origin and 0.001 to 0.02% of proteolytic enzyme of fungal origin previously dissolved in the kneading water;
iii) adding the microencapsulated bacteria consortium such that about $10^{10}$ CFU of the mixture of three strains of lactic-acid bacteria per gram of fluor is present;
iv) mixing; and
v) fermenting for 3 to 48 hours, preferably from 28 to 35 hours, at a temperature from 30 to 37° C., and a relative humidity from 70 to 92%, preferably 75 to 80%.

The flour used in step i) is selected from wheat flour, rye flour and oatmeal flour, preferably wheat flour.

Regarding fermentation, preferably this is carried out during 31 hours, at a temperature of 35° C. and a relative humidity of 76%.

As noted above, the sourdoughs of the present invention, obtained by the process noted above, have a gluten concentration lower than 20 ppm, preferably lower than 10 ppm. Preferably, this gluten concentration in the sourdoughs is achieved after 3 hours of fermentation.

From these sourdoughs it is possible to obtain baking products, preferably sweet bread, gluten-free, which are suitable for consumption by patients with celiac disease.

The present invention will be better understood from the following examples, which are presented with illustrative purposes only to allow a proper understanding of the preferred embodiments of the present invention, without implying that there are no other non-illustrated embodiments that can be practiced based on the above detailed description made.

EXAMPLES

Example 1

Inoculum Production

Strains of *Lactobacillus plantarum* ATCC 8014, *Lactobacillus brevis* ATCC 14869 and *Lactobacillus sanfranciscensis* ATCC 27652 were obtained through a supplier from the ATCC; the first two were preserved in a solid medium and the latter was lyophilized.

In order to reactivate the strains, seeds in liquid Man Rogosa Sharpe media (MRS) (Difco™, USA) were made in test tubes with a screw cap, incubating from 35 to 37° C. for 24 to 48 hours or until observing growth due to increased turbidity.

When the cultures had this feature, they were transferred to solid MRS medium in Petri dishes, incubating at the same temperature also over 24 to 48 hours.

Once the microorganisms grew up, they were transferred separately to a 125 mL Erlenmeyer flask with 50 ml of MRS medium, incubating for 8 to 12 hours at 37° C. with stirring at 50 to 100 rpm; this was the pre-inoculum.

After the incubation time the culture was transferred again, in aseptic conditions, to a 2800 mL Fembach flask with 500 to 1000 ml of MRS media, which was incubated at 37° C. and stirring at 50 to 150 rpm over 10 to 16 hours. Each flask was sampled to measure medium absorbance (turbidity).

In order to remove the remaining media and concentrate the microorganisms, the culture was placed in ethanol sanitized 250 mL centrifuge vials, and was then centrifuged at 2000 to 5000 rpm for 20 minutes.

The pellet obtained was resuspended in sterile saline (sodium chloride, 9 g/L). Once the microorganisms were re-suspended and the volume required adjusted, the inoculum to be microencapsulated was prepared also in aseptic conditions by mixing the required amounts of each strain and getting to the final volume.

Example 2

Micro-encapsulation of the Bacterial Consortium

Lactic serum isolated protein with 90% protein due to its barrier properties to oxygen, maltodextrin with a dextrose equivalent of 10 and Arabic gum were selected as encapsulating agents in different ratios.

To support reactivation of the bacteria in the consortium, the addition of three types of prebiotic agents was analyzed: polidextrose, inulin and maguey honey. Also, trehalose was used as a specific nutritional ingredient for the bacteria forming the consortium.

Encapsulating agents were dissolved in water at the proper ratios and to have 20% to 30% of dissolved solids. Prebiotics and trehalose were added, and this dispersion was inoculated with such amount of bacterial consortium so as to have $10^{10}$ CFU/g powder microencapsulated.

The previous mixture was dried by a spray-dryer, at an inlet temperature of 150° C. and an outlet one of 80° C., with a feed rate of 22 mL/min.

As a result, the powder microencapsulated microbial consortium was obtained.

Example 3

Prebiotic Ratios Determination Favoring Lactic-Acid Bacteria (BAL) Development

As mentioned above, the addition of polidextrose (P), inulin (I) and maguey honey (M) to the microencapsulated consortium was assessed. To that end, a single centroid mixture design was used in the experiment, as shown in Table 1:

TABLE 1

Prebiotic formulations assessed for microencapsulation of the microbial consortium

| Treatment | Prebiotic (g) | | |
|---|---|---|---|
| | P | I | M |
| 1 | 0.76 | 2.00 | 0.23 |
| 2 | 4.50 | 0 | 0 |
| 3 | 0 | 0 | 1.40 |
| 4 | 0 | 3.00 | 0 |
| 5 | 0 | 1.50 | 0.70 |
| 6 | 2.25 | 0 | 0.70 |

TABLE 1-continued

Prebiotic formulations assessed for microencapsulation of the microbial consortium

| Treatment | Prebiotic (g) | | |
|---|---|---|---|
| | P | I | M |
| 7 | 3.00 | 0.51 | 0.23 |
| 8 | 1.48 | 0.90 | 0.46 |
| 9 | 2.25 | 1.50 | 0 |
| 10 | 0.76 | 0.51 | 0.93 |
| 11 | 1.48 | 0.90 | 0.46 |

Each mixture was added to the corresponding LAB dispersion and wall material and dried by spraying, as described above.

Once the microencapsulated was obtained, 1 g of the powder was taken and rehydrated in sterile water to 30° C. with stirring. An aliquot of 1 ml was taken and serial dilutions were made, and plate seeding to determine the most probable number. The results of bacterial survival are shown in Table 2.

TABLE 2

Survival percentage of LAB depending on prebiotic combination

| Treatment | % LAB Survival |
|---|---|
| 1 | 84 |
| 2 | 60 |
| 3 | 98 |
| 4 | 70 |
| 5 | 75 |
| 6 | 80 |
| 7 | 72 |
| 8 | 78 |
| 9 | 60 |
| 10 | 80 |
| 11 | 85 |

According to the above, it can be seen that the greatest survival (98%) was reached when the prebiotic was maguey honey.

Example 4

Sourdoughs Preparation

White wheat flour commercially available, suitable for manual baking was used, as well as the microencapsulated bacterial consortium obtained according to Example 2, with a concentration of $10^{10}$ CFU/g, and in addition to encapsulating agents and trehalose, further containing maguey honey as a prebiotic.

As proteolytic enzymes, one of bacterial origin (HT proteolitic 200, Enmex S. A. de C. V., Mexico) and another one of fungal origin (Harizyme G, Enmex S. A. de C. V., Mexico) were used.

For sourdoughs preparation, the dough was prepared with an MY (mass yielding) between 150-160 from wheat flour, mixing 400 g flour, 150 mL of water. 0.08 g of proteolytic enzyme of bacterial origin (HT proteolitic 200, Enmex S. A. de C. V., Mexico) and 0.12 g of proteolytic enzyme of fungal origin (Harizyme G, Enmex S. A. de C. V., Mexico) were added, both previously dissolved in the kneading water. Subsequently, the microbial consortium micro-capsules of the present invention were added, suspended in water, in such a way to achieve $10^{10}$ CFU/g.

It was mixed for 8 min in a standard blender and then subjected to fermentation for 31 h at 35° C. and a relative humidity of 76%. pH during fermentation and the intensity of gluten degradation at the end of the fermentation were monitored by electrophoretic analysis (Western Blot test). The results are shown in Table 3.

TABLE 3

Kinetics of degradation of inoculated sourdoughs with the microencapsulated bacterial consortium

| | t1 | t2 | t3 | t4 | t5 | t6 | t7 |
|---|---|---|---|---|---|---|---|
| Type of inoculum | Powder | Powder | Powder | Powder | Powder | Powder | Powder |
| Time (h) | 3 | 6 | 7 | 11 | 23 | 27 | 31 |
| Gliadines (ppm) | 4.1 | 3.0 | <5.0 | <3.0 | 4.1 | <3.0 | <3.0 |
| Hordeines (ppm) | NA | NA | NA | NA | NA | NA | NA |
| Secalines (ppm) | NA | NA | NA | NA | NA | NA | NA |
| Areninas (ppm) | NA | NA | NA | NA | NA | NA | NA |

According to the data shown in the table, it is possible to see an intensive degradation of the gluten gliadin fraction by the effect of the microencapsulated bacterial consortium of the present invention, in combination with the proteolytic enzymes, within the first 3 hours of fermentation.

Example 5

Elaboration of Astorga Cupcake-Type Sweet Bread with Sourdoughs by Lactic-Acid Fermentation Cupcake-type, gluten-free, sweet bread was made using the sourdough obtained according to Example 4. To this end, butter, margarine and sugar glass were beat using the mixer palette, first at low speed until incorporation, and then increasing the speed and mixing for 20 more minutes to incorporate the largest amount of air into the mixture.

Three egg yolks were added little by little, until its complete incorporation, and subsequently milk, flavoring (orange, lime and chocolate) and potassium sorbate were added.

The fermented sourdough according to Example 4, maize starch, nixtamalized flour, baking soda and baking powder, pre-mixed in a plastic bag were incorporated to the previous mixture. Water was added and it was mixed at high speed for 8 minutes.

Separately, the egg whites were beat until stiff and then were blended in with the rest of the dough, at medium speed so as not to break the foam.

The fluid mass was deposited in cupcake paper cups in oven baking trays and it was baked for 10 minutes at 200° C.

Example 6

Astorga Cupcakes Assessment by Consumers

In order to determine the acceptability of the cupcakes with orange, lime and chocolate flavor, prepared according to Example 5 (using the sourdough obtained with the microencapsulated microbial consortium, in combination with proteolytic enzymes, of the present invention), compared to "natural" cupcakes made with traditional dough, an assessment was carried out among consumers.

To this end, a test was carried out with 70 consumers of Astorga cupcakes from the Universidad Iberoamericana, Mexico City campus. The participants, 50% men and 50% women, aged from 15 to over 45, were consumers of commercial sweet bread consuming at least every 15 days. The significance and confidence level of the test is 0.05% and 95%, respectively. The results are shown in Table 4.

TABLE 4

Test Results with consumers of cupcakes made from fermented sourdough with microencapsulated bacterial consortium in combination with proteases.

| Cupcake | Appearance | Texture Range: 1-5 (1 least pleasant, 5 most pleasant) | Flavor | General acceptance Range: 1-5 (1 least pleasant, 5 most pleasant) |
|---|---|---|---|---|
| Natural$_a$ | 4.01$_a$ Good | 3.87$_a$ Good | 4.04$_a$ Good | 7.96$_a$ |
| Orange flavor$_b$ | 3.9$_{ab}$ Good | 3.99$_{ab}$ Good | 4.00$_{ab}$ Good | 8.1$_{ab}$ |
| Chocolate flavor$_c$ | 3.77$_{ac}$ Almost good | 3.89$_{ac}$ Good | 3.76$_{ac}$ Almost good | 7.64$_{ac}$ |
| Lime flavor$_d$ | 3.41$_d$ Between regular and good | 3.56$_d$ Between good and regular | 3.26$_d$ Regular | 6.81$_d$ |

The results in Table 4 show that there is not a significant difference in 95% (0.05) with respect to the natural cupcake in all the assessed attributes (appearance, texture and flavor) and in general acceptance of cupcakes with orange flavor and chocolate flavor.

On the contrary, the lime cupcake does present significant difference at 95% with respect to the natural cupcake in all the assessed attributes, in favor of the natural cupcake.

In accordance with the above-described, it will be observed that the microencapsulated bacterial consortium for gluten degradation in sourdoughs and the process of making the same, as well as the baked products obtained from such sourdoughs, have been devised to have gluten-free products, that might be suitable for consumption by celiac patients, and it will be apparent to any expert in the art that the described embodiments of the microencapsulated consortium for gluten degradation in sourdoughs and the process of making thereof as described, are only illustrative and non-limiting of the present invention, since various changes of consideration are possible in their details without departing from the scope of the invention.

Therefore, the present invention should not be considered restricted except for what is demanded by the prior art and by the scope of the appended claims.

What is claimed is:

1. A microencapsulated bacterial consortium for gluten degradation comprising:
   (a) the following three different species of lactic-acid bacteria:
   Lactobacillus plantarum ATCC 8014,
   Lactobacillus sanfranciscensis ATCC 27652 and
   Lactobacillus brevis ATCC 14869,
   and no other species of lactic acid bacteria;
   b) encapsulating agents;
   c) prebiotics; and
   d) trehalose;
   in combination with a proteolytic enzyme of bacterial origin and a proteolytic enzyme of fungal origin.

2. A microencapsulated bacterial consortium, according to claim 1, wherein the encapsulating agents are selected from the group consisting of isolated protein from milk serum with 90% protein, maltodextrin with a dextrose equivalent of 10, arabic gum, mesquite gum, sodium alginate, pectin, soy isolated protein, casein and combinations thereof.

3. A microencapsulated bacterial consortium, according to claim 2, wherein the encapsulating agents are isolated protein from milk serum with 90% protein, maltodextrin with a dextrose equivalent of 10, arabic gum and combinations thereof.

4. A microencapsulated bacterial consortium, according to claim 1, wherein the prebiotics are selected from the group consisting of polydextrose, inulin and maguey honey.

5. A microencapsulated bacterial consortium, according to claim 4, wherein the prebiotic is maguey honey.

6. A microencapsulated bacterial consortium, according to claim 1, wherein the proteolytic enzyme of bacterial origin and the proteolytic enzyme of fungal origin are selected from enzymes commonly used for baking.

7. A microencapsulated bacterial consortium, according to claim 1, comprising: a) *Lactobacillus plantarum* ATCC 8014; b) *Lactobacillus sanfranciscensis* ATCC 27652; c) *Lactobacillus brevis* ATCC 14869; d) isolated protein from milk serum with 90% protein; e) maltodextrin with a dextrose equivalent of 10; f) arabic gum; g) maguey honey; and h) trehalose;
in combination with a proteolytic enzyme of bacterial origin and a proteolytic enzyme of fungal origin.

8. A microencapsulated bacterial consortium, according to claim 7, comprising: a) *Lactobacillus plantarum* ATCC 8014; b) *Lactobacillus sanfranciscensis* ATCC 27652; c) *Lactobacillus brevis* ATCC 14869; d) from 40 to 60% of isolated protein from milk serum with 90% protein; e) from 10 to 20% of maltodextrin with a dextrose equivalent of 10; f) from 20 to 80% arabic gum; g) from 1 to 10% of maguey honey; and h) trehalose;
in combination with 0.005 to 0.03% of a proteolytic enzyme of bacterial origin and 0.001 to 0.02% of a proteolytic enzyme of fungal origin.

9. A process for producing a microencapsulated bacterial consortium for gluten degradation, comprising the steps of:
a) separately reactivating each strain of lactic-acid bacteria;
b) when each strain is active, separately culturing in a liquid culture medium until achieving each strain desired concentration;
c) for each strain, removing the excess culture medium to concentrate the microorganisms, obtaining a pellet;
d) separately, resuspending the pellet obtained for each strain in saline suspension and adjusting to the required volume;
e) mixing the necessary amounts of each strain and taking to a final volume;
f) dissolving the encapsulating agents in water, at the proper ratios to have 20 to 30% of dissolved solids;
g) adding prebiotics and trehalose;
h) inoculating with the mixture of the three strains of lactic-acid bacteria, such that about $10^{10}$ CFU of said mixture of three strains of lactic-acid bacteria per gram of powdered microencapsulated are obtained; and
i) drying, to an inlet temperature of between 110 and 160° C., and an outlet temperature of between 60 and 80° C., with a feed rate between 20 and 50 mL/min.

10. A process for producing a microencapsulated bacterial consortium, according to claim 9, wherein the drying is carried out by a spray-dryer, at an inlet temperature of 150° C., and at an outlet temperature of 80° C., with a feed rate of 22 mL/min.

11. A process to make a sourdough from a microencapsulated bacterial consortium for gluten degradation, in combination with a proteolytic enzyme of bacterial origin and a proteolytic enzyme of fungal origin, comprising the following steps:
i) mixing 30 to 60% flour with 40 to 80% water to obtain a dough with a dough yield (DY) from 150 to 475;
ii) adding 0.005 to 0.03% proteolytic enzyme of bacterial origin and 0.001 to 0.02% proteolytic enzyme of fungal origin previously dissolved in kneading water;
iii) adding the microencapsulated bacterial consortium such that about $10^{10}$ CFU/g flour is present;
iv) mixing; and
v) fermenting for 3 to 48 hours, at a temperature from 30 to 37° C., and a relative humidity from 70 to 92%.

12. A process to make a sourdough, according to claim 11, wherein the flour used in step i) is selected from wheat flour, rye flour and oatmeal flour.

13. A process to make a dough sour, according to claim 12, wherein the flour is wheat flour.

14. A process to make a sourdough, according to claim 11, wherein the fermentation is carried out during 31 hours, at a temperature of 35° C. and a relative humidity of 76%.

15. A process for producing a microencapsulated bacterial consortium, according to claim 9, wherein in step c) the excess culture medium is removed by centrifugation.

16. A process to make a sourdough, according to claim 11, wherein in step i) the dough obtained has a dough yield (DY) from 150 to 160.

17. A process to make a sourdough, according to claim 11, wherein in step v) the fermentation is carried out for 28 to 35 hours.

18. A process to make a sourdough, according to claim 11, wherein in step v) the fermentation is carried out at a relative humidity from 75 to 80%.

* * * * *